United States Patent [19]

Kosa et al.

[11] 4,287,194

[45] Sep. 1, 1981

[54] COMPOSITIONS WITH POTENTIATED HYPOTENSIVE EFFECTS

[75] Inventors: Edit Kósa; János Borvendég; Zsuzsanna Huszti; Judit Kosáry; Géza Szilágyi; László Tardos; Endre Kasztreiner; László Nagy; Erzsébet Szuücs; Gabriella Kiss, all of Budapest, Hungary

[73] Assignee: Richter Gedeon Vegyészeti Gyár Rt., Budapest, Hungary

[21] Appl. No.: 55,263

[22] Filed: Jul. 6, 1979

[30] Foreign Application Priority Data

Jul. 14, 1978 [HU] Hungary ............... GO 1412

[51] Int. Cl.³ ............... A61K 31/535; A61K 31/495; A61K 31/40; A61K 31/235
[52] U.S. Cl. ............... 424/248.51; 424/250; 424/274; 424/308; 424/309; 424/310
[58] Field of Search ............... 424/248.51, 250, 274, 424/308, 309, 310, 319

[56] References Cited

U.S. PATENT DOCUMENTS 3,462,536   8/1969   Chemerda ............... 424/309

FOREIGN PATENT DOCUMENTS 868027 12/1978 Belgium ............... 424/248

OTHER PUBLICATIONS

Huszti, Biochem Pharm, vol. 22, 1973, p. 2253.
Prichard et al., British Med. J., Jan. 4, 1969 [L] pp. 7–16.

*Primary Examiner*—Anna P. Fagelson
*Attorney, Agent, or Firm*—Karl F. Ross

[57] ABSTRACT

A pharmaceutical compositions with hypotensive effects which comprise a compound of formula (I) or a pharmaceutically acceptable acid addition salt thereof, $$R^1-N\begin{array}{c}R^2\\R^3\end{array} \quad (I)$$

wherein
$R^1$ is formula (II)

$$R^4\text{-phenyl-}CH_2-O- \quad (II)$$
(with $R^5$ on phenyl)

wherein
$R^4$ and $R^5$ each represent hydrogen, hydroxy, nitro at the same time
$R^2$ and $R^3$ are hydrogen, or
$R^1$ are 3-chloro-6-pyridazinylamino, 3-methyl-6-pyridazinylamino or 3-carbamoyl-6-pyridazinylamino, and at the same time
$R^2$ and $R^3$ form together formula (III), $$=C\begin{array}{c}R^6\\(CH_2)_n-CO_2R^7\end{array} \quad (III)$$

wherein
$R^6$ is $C_{1-4}$ alkyl group,
$R^7$ is hydrogen or a $C_{1-4}$ alkyl group, and
n is an integer of 1 to 3, or
$R^2$ and $R^3$ form together a group of the general formula (IV), $$=Q-R^8 \quad (IV)$$

wherein
Q is $C_{5-7}$ cycloaliphatic, and
$R^8$ is hydrogen, a $C_{1-4}$ alkoxycarbonyl or a $C_{2-4}$ alkyl, and a compound of formula (V) or a pharmaceutically acceptable acid addition salt thereof, $$R^9-O-CH_2-\underset{OH}{\overset{|}{CH}}-CH_2-NHR^{10} \quad (V)$$

wherein
$R^9$ is naphthyl, 4-indolyl or 4-morpholino-1,2,5-thiadiazol-3-yl group or $$R^{11}\text{-phenyl} \quad (VI)$$
(with $R^{12}$, $R^{13}$ on phenyl)

13 Claims, No Drawings

COMPOSITIONS WITH POTENTIATED HYPOTENSIVE EFFECTS

FIELD OF THE INVENTION

This invention relates to pharmaceutical compositions with increased hypotensive effects as well as to a process for the preparation thereof.

BACKGROUND OF THE INVENTION

Compounds which exert a blocking effect on β-adrenergic receptors are have found increasingly widespread acceptance in the treatment of hypertension (Knoll J.: *Gyogyszertan, Medicina*, p. 282, 1971); S. Wolfson: *Drugs in Cardiology* Vol. I, pp. 165-179, (Stratton Intercont. Med. Book Corp., New York, 1975; R. P. Ahlquist: *Progress in Drug Research* 20, pp. 27-42, (Birkhäuser Verlag, Basel, 1976). Their use is, however, restricted by several contraindications, such as respiratory disease (bronchial asthma), cardiovascular disease (bradycardia, heart block), renal inflammation and metabolic disorder, e.g. diabetes mellitus and liver disease (R. P. Ahlquist: *Beta-Adrenergic Blocking Agents in the Management of Hypertension and Angina Pectoris*, pp. 1-81, Raven Press, New York, 1974). The dosages required in the treatment of hypertension are 4 to 8 times higher than those provoking antiarrhythmic effects (A. Ablad: *Drugs*, 11, Suppl. 1, pp. 127-134, 1976), which may give rise to the appearance of more severe side effects, such as bronchial spasms, cardiac disorders, central nervous-system effects (hallucinations, insomnia, depression), Raynaud-syndrome and gastrointestinal disorders (D. J. Greenblatt: *Drugs*, 7, 118, 1974; S. A. Stephen: *Am. J. Cardiol.* 18, 463, 1966). A further characteristic feature of β-receptor blocking agents is that, beyond a certain limit, their therapeutic effect cannot be incresed by increasing the dosage (P. Kincaid-Smith: *Beta-Adrenergic Blocking Agents in the Management of Hypertension and Angina Pectoris*, pp. 9-19 (Raven Press, New York, (1974).

OBJECT OF THE INVENTION

The invention has the object of providing a novel pharmaceutical composition, free from the disadvantages discussed above, which exerts beneficial therapeutic effects in much lower dosages than the hitherto known ones and causes much weaker undesired side effects, if any, than conventional β-receptor blocking agents.

DESCRIPTION OF THE INVENTION

The invention is based on the surprising discovery that compounds of formula (I), below, which, when applied alone, exert a blocking effect on the biosynthesis of noradrenaline (decarboxylase, tyrosine hydroxylase and dopamine-β-hydroxylase blocking effects, see Zs. Huszti: *Biochem. Pharm.* 22, 2253 (1973) and Belgian Pat. No. 868,027), considerably potentiate the hypotensive effect of the β-adrenergic receptor blocking agents having formula (V), infra.

Based on the above, the invention provides pharmaceutical compositions with increased hypotensive effects, comprising a compound of formula (I),

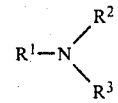

wherein
$R^1$ is a group of formula (II),

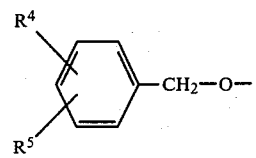

(wherein $R^4$ and $R^5$ each can be hydrogen, hydroxy, nitro or $C_{1-4}$ alkoxycarbonyl), and at the same time $R^2$ and $R^3$ are each hydrogen, or
$R^1$ is 3-chloro-6-pyridazinylamino, 3-methyl-6-pyridazinylamino or 3-carbamoyl-6-pyridazinylamino group, and at the same time $R^2$ and $R^3$ form together a group of formula (III),

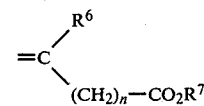

wherein
$R^6$ is $C_{1-4}$ alkyl,
$R^7$ is hydrogen or $C_{1-4}$ alkyl, and
n is an integer of 1 to 3, or
$R^2$ and $R^3$ form together a group of formula (IV),

wherein
Q is $C_{5-7}$ cycloaliphatic group, and
$R^8$ is hydrogen, $C_{1-4}$ alkoxycarbonyl or $C_{2-4}$ alkyl, and a compound of formula (V) or a salt thereof,

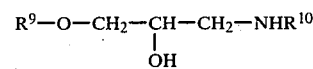

wherein
$R^9$ is naphthyl, 4-indolyl or 4-morpholino-1,2,5-thiadiazol-3-yl group or a group of formula (VI),

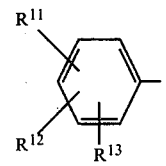

wherein
$R^{11}$, $R^{12}$ and $R^{13}$ are the same or different and represent hydrogen, halogen, hydroxy, $C_{1-4}$ alkyl, $C_{1-4}$ alkoxy, $C_{2-4}$ alkenyloxy, 2-methoxyethyl or acetic amide, with the proviso that when two of $R^{11}$, $R^{12}$ and $R^{13}$ are hydrogen, the third substituent is other than hydrogen, and when two of $R^{11}$, $R^{12}$ and $R^{13}$ are acetic amide, the third substituent is other than acetic amide, and $R^{10}$ stands for $C_{1-4}$ alkyl, in admixture with one or more conventional pharmaceutical additives.

The invention relates further to a process for the preparation of novel pharmaceutical compositions with increased hypotensive effects. According to the invention a compoun of formula (I) is admixed with a compound of formula (V) and the mixture is converted into pharmaceutical dosage forms, such as tablets, suppositories, etc., utilizing conventional pharmaceutical additives.

A preferred pharmaceutical composition according to the invention comprises 1 part by weight of 1-(4-indolyloxy)-3-isopropylamino-2-propanol hydrochloride (further: pindolol) in admixture with 20 parts by weight of 3-hydroxy-4-nitro-benzyloxyamine hydrochloride (further: compound 11,130).

Another preferred composition comprises 1 part by weight of pindolol in admixture with 40 parts by weight of 2-hydroxy-5-carbomethoxy-benzyloxyamine hydrochloride (further: compound 11,121).

Other preferred compositions according to the invention contain as β-adrenergic receptor blocking agent a compound listed in Table 1, together with a noradrenaline biosynthesis blocking compound as listed in Table 2 or a salt thereof.

TABLE 1

| Chemical name | International name or protected name |
|---|---|
| 1-(1-Naphthyloxy)-3-isopropylamino-2-propanol hydrochloride | Propranolol |
| 1-(2,5-Dichlorophenoxy)-3-tert.-butyl-amino-2-propanol hydrochloride | Tobanum |
| 1-(4-[2-Methoxyethyl]-phenoxy)-3-isopropylamino-2-propanol hydrochloride | Metoprolol |
| 1-(4-Aminocarbonylmethyl-phenoxy)-3-isopropylamino-2-propanol hydrochloride | Atenolol |
| 1-(2-Allyloxy-phenoxy)-3-isopropyl-amino-2-propanol hydrochloride | Oxprenolol |

TABLE 2

| Chemical name | Code No. (Compound) |
|---|---|
| $N^1$-(3-Chloro-6-pyridazinyl)-$N^2$-(1-carbethoxy-2-propylidene)-hydrazine | 11,473 |
| $N^1$-(3-Chloro-6-pyridazinyl)-$N^2$-(1-carbethoxy-2-cyclohexylidene)-hydrazine | 11,511 |
| $N^1$-(3-Chloro-6-pyridazinyl)-$N^2$-(2,2-methyl-1-cyclohexylidene)-hydrazine | 11,588 |
| $N^1$-(3-chloro-6-pyridazinyl)-$N^2$-(1-tert.-carbobutoxy-2-propylidene)-hydrazine | 11,653 |
| $N^1$-(3-Carbamoyl-6-pyridazinyl)$N^2$-(1-tert.-carbobutoxy-2-propylidene)-hydrazine | 11,702 |
| $N^1$-(3-Methyl-6-pyridazinyl)-$N^2$-(1-tert.-carbobutoxy-2-propylidene)-hydrazine | 11,741 |

The compositions according to the invention contain the β-receptor blocking agents in lower dosages than the conventional dosage, thus the undesired side effects of these compounds can be suppressed considerably. Another advantage of the new compositions is that the noradrenaline biosynthesis blocking compounds applied potentiate the hypotensive effects of the β-receptor blocking agents, i.e. the hypotensive effect of the composition greatly exceeds the algebraic sum of the activities of the individual constituents.

The favorable effects of the new hypotensive compositions according to the invention are demonostrated by the pharmaceutical test results described below.

(1) Determination of the hypotensive effect on awake rats suffering from genetic hypertension The tests were performed according to the method of Eaton (J. C. R. Eaton: *Brit. J. Pharm.* 54, 282 (1975) with the modification that the blood pressure and cardiac frequency of Wistar-Okamoto rats were measured with an automatic five-channel instrument. The compounds and dosages applied, as well as the test results are listed in Tables 3 to 6.

The data of Tables 3 to 5 demonstrate the beneficial results obtained by administering pindolol in combination with a noradrenaline biosynthesis blocking agent.

TABLE 3

Effect of pindolol, compound 11,130 and combinations thereof on the blood pressure of genetically hypertensive awake rats

| | | | Blood pressure (mm Hg) | | | |
|---|---|---|---|---|---|---|
| Compound | Dosage mg/kg p.o. | No. of animals | Basal value | After 2 hours | After 5 hours | After 24 hours |
| Pindolol | 0.25 | 10 | 182.2 ±23.4 | 180.8 ±48.2 | 164.9 ±28.7 | 183.4 ±46.2 |
| Pindolol 11,130 | 0.25 20 | 5 | 161.0 ±10.8 | 140.0* ±11.7 | 146.0 ±12.4 | 153.0 ±20.8 |
| Pindolol | 0.5 | 15 | 165.0 ±14.2 | 161.4 ±18.6 | 160.5 ±22.2 | 150.5 ±22.4 |
| Pindolol 11,130 | 0.5 20 | 15 | 173.2 ±17.6 | 128.2**** ±34.7 | 123.6**** ±24.1 | 159.3 ±26.2 |
| Pindolol | 1.0 | 10 | 164.4 ±13.8 | 135.0*** ±20.5 | 135.0*** ±16.9 | 151.1 ±22.2 |
| Pindolol | 5.0 | 10 | 172.5 ±14.4 | 154.5*** ±8.0 | 124.5**** ±15.0 | 161.0 ±20.5 |
| 11,130 | 20 | 5 | 174.0 ±12.9 | 183.0 ±18.2 | 176.0 ±10.2 | 172.0 ±14.4 |

\* = 0.05 > p > 0.02
\*\* = 0.02 > p > 0.01
\*\*\* = 0.01 > p > 0.001
\*\*\*\* = 0.001 > p p = statistical significance (R.A. Fisher: "Statistical Methods for Research Workers", Oliver and Boyd, London, 1950)
ED$_{30\%}$ p.o. ~ 5 mg/kg of pindolol
ED$_{30\%}$ p.o. ~ 0.5 mg/kg of pindolol + 20 mg/kg of 11,130
(ED$_{30\%}$ is the dosage which decreases the blood pressure by 30% related to the value before treatment)

The test results listed in Table 3 indicate that the ED$_{30\%}$ of pindolol (5 mg/kg) can be decreased to one-tenth upon combining this compound with 11,130.

TABLE 4

Effect of pindolol, 11,121 and combinations thereof on the blood pressure of genetically hypertensive awake rats

| | | | Blood pressure (mmHg) | | | |
|---|---|---|---|---|---|---|
| Compound | Dosage mg/kg p.o. | No. of animals | Basal value | After 2 hours | After 5 hours | After 24 hours |
| Pindolol | 0.25 | 10 | 184.4 ±29.4 | 181.6 ±28.8 | 168.8 ±18.9 | 188.8 ±46.8 |
| Pindolol 11,121 | 0.25 5 | 10 | 199.4 ±41.7 | 151.7** ±26.3 | 178.8 ±49.2 | 183.3 ±40.3 |
| Pindolol 11,121 | 0.25 10 | 10 | 182.2 ±26 | 165.0 ±28.3 | 138.9*** ±23.2 | 175.0 ±9.7 |
| Pindolol | 0.5 | 10 | 200.0 ±31.8 | 191.2 ±7.9 | 188.3 ±36.4 | 188.9 ±38.4 |
| Pindolol 11,121 | 0.5 5 | 10 | 208.7 ±40.1 | 156.7* ±48.8 | 150.4** ±44.0 | 192.9 ±51.7 |
| Pindolol 11,121 | 0.5 20 | 10 | 160.5 ±21.1 | 112.2*** ±32.1 | 112.7*** ±23.7 | 146.7 ±24.4 |
| Pindolol | 1 | 10 | 164.4 ±13.8 | 135.0*** ±20.5 | 135.0*** ±16.9 | 151.1 ±22.2 |
| Pindolol | 5 | 10 | 172.5 ±14.4 | 154.5*** ±8.0 | 124.5**** ±15.0 | 161.0 ±20.5 |
| 11,121 | 50 | 5 | 168.2 | 170.0 | 163.0 | 169.0 |

TABLE 4-continued

Effect of pindolol, 11,121 and combinations thereof on the blood pressure of genetically hypertensive awake rats

| Compound | Dosage mg/kg p.o. | No. of animals | Basal value | After 2 hours | After 5 hours | After 24 hours |
|---|---|---|---|---|---|---|
| | | | ±10.4 | ±11.2 | ±17.8 | ±13.4 |

\* = 0.05 > p > 0.02
\*\* = 0.02 > p > 0.01
\*\*\* = 0.01 > p > 0.001
\*\*\*\* = 0.001 > p
$ED_{30\%}$ p.o. ~ 5 mg/kg of pindolol
$ED_{30\%}$ p.o. ~ 0.5 mg/kg of pindolol + 20 mg/kg of 11,121

The test results listed in Table 4 indicate that the combined administration of 11,121 and pindolol causes an approximately tenfold increase in the activity of pindolol. Thus the combinations of these compounds can be applied to advantage in therapy.

TABLE 5

Effect of pindolol, 11,473 and combinations thereof on the blood pressure of genetically hypertensive awake rats

| Compound | Dosage mg/kg p.o. | No. of animals | Basal value | After 2 hours | After 5 hours | After 24 hours |
|---|---|---|---|---|---|---|
| Pindolol | 0.5 | 15 | 200.3 ±30.5 | 172.1* ±36.9 | 160.8* ±46.9 | 188.6 ±30.2 |
| Pindolol 11,473 | 0.5 5 | 15 | 196.0 ±35.3 | 159.6** ±33.5 | 141.3** ±48.3 | 179.9 ±28.1 |
| Pindolol 11,473 | 0.5 10 | 15 | 205.3 ±23.3 | 149.3*** ±40.1 | 138.2**** ±32.9 | 191.3 ±42 |
| Pindolol | 1 | 10 | 164.4 ±13.8 | 135.0*** ±20.5 | 135.0*** ±16.9 | 151.1 ±22.2 |
| Pindolol | 5 | 10 | 172.5 ±14.4 | 154.5*** ±8.0 | 124.5**** ±15.0 | 161.0 ±20.5 |
| 11,473 | 10 | 5 | 195.0 ±11.2 | 194.0 ±8.2 | 197.0 ±7.6 | 198.0 ±9.1 |

\* = 0.05 > p > 0.02
\*\* = 0.02 > p > 0.01
\*\*\* = 0.01 > p > 0.001
\*\*\*\* = 0.001 > p
$ED_{30\%}$ p.o. ~ 5 mg/kg of pindolol
$ED_{30\%}$ p.o. ~ 0.5 mg/kg of pindolol + 10 mg/kg of 11,473

The test results listed in Table 5 indicate that the required dosage of pindolol can be decreased to about one tenth by administering it in combination with 11,473. Thus the combinations of these compounds can be applied to advantage in therapy.

The hypotensive effect of propranolol can also be increased by combining it with a noradrenaline biosynthesis blocking agent, such as 11,130. The test results are given in Table 6.

TABLE 6

Effect of propranolol, 11,130 and combinations thereof on the blood pressure of genetically hypertensive awake rats

| Compound | Dosage mg/kg p.o. | No. of animals | Basal value | After 2 hours | After 5 hours | After 24 hours |
|---|---|---|---|---|---|---|
| Propranolol | 1 | 5 | 167.5 ±12.6 | 170.0 ±12.9 | 168.7 ±13.8 | 157.5 ±8.7 |
| Propranolol 11,130 | 1 20 | 15 | 169.5 ±21.0 | 161.9 ±26.0 | 146.1* ±19.7 | 163.9 ±23.1 |
| Propranolol | 5 | 10 | 186.4 ±13.6 | 178.6 ±13.4 | 175.9 ±24.3 | 181.8 ±16.8 |
| Propranolol 11,130 | 10 20 | 15 | 178.0 ±16.1 | 170.0 ±15.2 | 148.3* ±18.6 | 163.7 ±24.7 |
| 11,130 | 20 | 5 | 174.0 ±12.9 | 183.0 ±18.2 | 176.0 ±10.2 | 172.0 ±14.4 |

\* = 0.001 > p
$ED_{15\%}$ p.o. ~ 10 mg/kg of propranolol
$ED_{15\%}$ p.o. ~ 1 mg/kg of propranolol + 20 mg/kg of 11,130

The test results listed in Table 6 indicate that the combined administration of propranolol and 11,130 causes an about tenfold increase in the activity of the β-receptor blocking component.

(2) Determination of the hypotensive effect on awake dogs suffering from renal hypertension The tests were performed on dogs suffering from renal hypertension, subjected to operation as described by Grollman (A. Grollman: Proc. Soc. Exp. Biol. Med. 57, 102 (1944). The effects were determined by measuring the blood pressure on the caudal artery and the pulse rate. The test results obtained with pindolol, 11,121 and a combination thereof are listed in Table 7.

The data of Table 7 indicate that the hypotensive character of pindolol also changes favorably when using dogs as test animals.

TABLE 7

Effect of pindolol, 11,121 and a combination thereof on the blood pressure of awake dogs with renal hypertension

| Compound | Dosage mg/kg p.o. | No. of animals | Basal value | After 1 hour | After 2 hours | After 3 hours | After 4 hours | After 5 hours | After 24 hours |
|---|---|---|---|---|---|---|---|---|---|
| Pindolol | 0.1 | 3 | 156.7 ±15.3 | 133.3 ±11.5 | 133.3 ±17.6 | 153.0 ±5.8 | 156.7 ±2.9 | 160.0 ±5.0 | 153.3 ±11.5 |
| 11,121 | 5 | 3 | 165.0 ±5.8 | 170.0 ±7.6 | 167.5 ±10.4 | 175.0 ±5.0 | 165.0 ±5.0 | 172.5 ±7.6 | 165.0 ±2.9 |
| Pindolol 11,121 | 0.1 5 | 4 | 160.0 ±20.9 | 130.0 ±30.8 | 111.2* ±16.5 | 143.7 ±21.4 | 148.7 ±13.1 | 160.0 ±8.2 | 157.5 ±15.5 |

\* = 0.05 > p > 0.02

(3) Toxicity tests

Based on the data given in points 1 and 2 above it can be stated that a considerable potentiating synergism appears with respect to the hypotensive effect when applying the compounds of formula (I) in combination with those of formula (V). In the following it was investigated whether this synergism also appears with respect to the toxicity. In the first test series the $LD_{50}$ values of the individual components were determined on CFLP-mice. The compounds were administered orally, and the animals were kept under observation for one week. The $LD_{50}$ values of the individual compounds are as follows:

Pindolol: $LD_{50} = 300$ mg/kg p.o.
11,121: $LD_{50} = 2900$ mg/kg p.o.
11,473: $LD_{50} = 360$ mg/kg p.o.

To determine the toxicity values of the combinations dosages calculated on the basis of the isobole construction principle were applied. The animals were pre-treated for one hour with various dosages of 11,473 or 11,121, and then varying dosages of pindolol were administered. The results are listed in Table 8.

The data of Table 8 indicate that a pre-treatment with 100 or 200 mg/kg of 11,473, or with 100 or 1000 mg/kg of 11,121 hardly influences the toxicity of pindolol, thus there is no undesired potentiation of toxicity.

TABLE 8

Toxicity values of pindolol + 11,473 and pindolol + 11,121

| Pindolol mg/kg p.o. | Pindolol alone | 11,473 p.o. 100 mg/kg | 11,473 p.o. 200 mg/kg | 11,473 p.o. 300 mg/kg | 11,121 p.o. 100 mg/kg | 11,121 p.o. 1000 mg/kg | 11,121 p.o. 2000 mg/kg |
|---|---|---|---|---|---|---|---|
| 60  | 0  | 0  | 0  | 50 | 0  | 0  | 30 |
| 90  | 0  | 0  | 0  | 50 | 0  | 0  | 40 |
| 135 | 8  | 0  | 0  | 70 | 0  | 0  | 40 |
| 200 | 16 | 20 | 20 | —  | 0  | 10 | 30 |
| 300 | 46 | 40 | 70 | —  | 50 | 30 | 40 |
| 450 | 75 | 70 | —  | —  | 80 | 45 | 80 |

Mortality (%)

The test results prove unambiguously that the new combinations according to the invention enable one to use the active agents in lower amounts or in more effective forms with a high security.

The invention is elucidated in detail by the aid of the following non-limiting Examples.

EXAMPLE 1

Preparation of tablets

Composition of one tablet:

| Pindolol | 2.5 mg |
|---|---|
| 11,121 | 100.0 mg |
| Microcrystalline cellulose | 88.5 mg |
| Magnesium stearate | 2.0 mg |
| Talc | 6.0 mg |
| Colloidal silicon dioxide | 1.0 mg |

The tablets, weighing 200 mg in average, are provided with film coating.

EXAMPLE 2

Preparation of capsules

Composition of one capsule:

| Pindolol | 2.5 mg |
|---|---|
| 11,473 | 100.0 mg |
| Talc | 3.0 mg |
| Magnesium stearate | 2.0 mg |
| Colloidal silicon dioxide | 0.5 mg |

The mixture is filled into self-closing hard gelatine capsules. One capsule contains 108 mg of the above mixture in average.

EXAMPLE 3

Preparation of tablets

Composition of one tablet:

| Propranolol | 3.0 mg |
|---|---|
| 11,653 | 100.0 mg |
| Microcrystalline cellulose | 88.5 mg |
| Magnesium stearate | 2.0 mg |
| Talc | 6.0 mg |
| Colloidal silicon dioxide | 1.0 mg |

EXAMPLE 4

Preparation of tablets

Composition of one tablet:

| Atenolol | 2.5 mg |
|---|---|
| 11,702 | 80.0 mg |
| Microcrystalline cellulose | 80.0 mg |
| Magnesium stearate | 2.0 mg |
| Talc | 6.0 mg |
| Colloidal silicon dioxide | 1.0 mg |

What we claim is:

1. A pharmaceutical composition with increased hypotensive effect, comprising a compound of formula (I) or a pharmaceutically acceptable acid addition salt thereof, $$R^1-N\begin{matrix}R^2\\R^3\end{matrix} \quad (I)$$

wherein
$R^1$ is a group of formula (II),

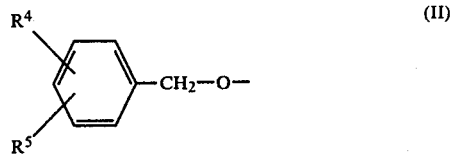

wherein
$R^4$ and $R^5$ each are hydrogen, hydroxy, nitro or $C_{1-4}$ alkoxycarbonyl, and at the same time
$R^2$ and $R^3$ each are hydrogen, or
$R^1$ is 3-chloro-6-pyridazinylamino, 3-methyl-6-pyridazinylamino or 3-carbamoyl-6-pyridazinylamino group, and at the same time
$R^2$ and $R^3$ form together a group of formula (III), $$=C\begin{matrix}R^6\\(CH_2)_n-CO_2R^7\end{matrix} \quad (III)$$

wherein
$R^6$ is $C_{1-4}$ alkyl group,
$R^7$ is hydrogen or a $C_{1-4}$ alkyl group, and
n is an integer of 1 to 3, or
$R^2$ and $R^3$ form together a group of formula (IV), $$=Q-R^8 \quad (IV)$$

wherein
Q is a $C_{5-7}$ cycloaliphatic group, and
$R^8$ is hydrogen, $C_{1-4}$ alkoxycarbonyl or $C_{2-4}$ alkyl;
and a β receptor blocking compound of formula (V) or a salt thereof,

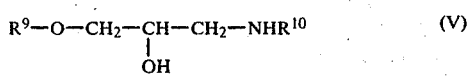 (V)

wherein
R$^9$ stands for naphthyl, 4-indolyl or 4-morpholino-1,2,5-thiadiazol-3-yl group or a group of formula (VI),

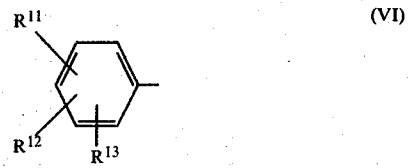 (VI)

wherein
R$^{11}$, R$^{12}$ and R$^{13}$ are the same or different and represent hydrogen, halogen, hydroxy, C$_{1-4}$ alkyl, C$_{1-4}$ alkoxy, C$_{2-4}$ alkenyloxy, 2-methoxyethyl or acetic amide; but that when two of R$^{11}$, R$^{12}$ and R$^{13}$ are hydrogen, the third is other than hydrogen, or when two of R$^{11}$, R$^{12}$ and R$^{13}$ are acetic amide, the third is other than acetic amide, and R$^{10}$ stands for C$_{1-4}$ alkyl, in admixture with at least one conventional pharmaceutical additives, wherein the compound of formula I is a hypotensive potentiating agent present in an effective amount to potentiate the β receptor blocking compound of V.

2. A composition as claimed in claim 1, comprising 3-hydroxy-4-nitro-benzyloxyamine hydrochloride as the compound of formula (I).

3. A composition as claimed in claim 1, comprising 2-hydroxy-5-carbomethoxy-benzyloxyamine hydrochloride as the compound of formula (I).

4. A composition as claimed in claim 1, comprising 3-(ethoxycarbonyl)-2-propylidene-(3-chloro-6-pyridazinyl)-hydrazine as the compound of formula (I).

5. A composition as claimed in claim 1, comprising 1-(4-indolyloxy)-3-isopropylamino-2-propanol hydrochloride as the compound of formula (V).

6. A composition as claimed in claim 1, comprising 1-(1-naphthyloxy)-3-isopropylamino-2-propanol hydrochloride as the compound formula (V).

7. A method of treating hypotension in animal subjects which comprises administering an antihypertensive effective amount of a composition as defined in claim 1, claim 2 or claim 5.

8. A pharmaceutical composition with hypotensive effect, comprising a compound of the formula I or a pharmaceutically acceptable salt thereof

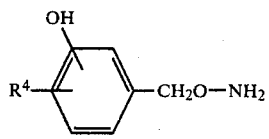

wherein R$^4$ is nitro or C$_1$ to C$_4$ alkoxycarbonyl and a β receptor blocking compound of the formula V or a pharmaceutically acceptable salt thereof

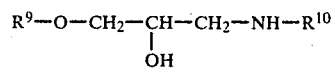

wherein
R$^9$ is naphthyl, 4-indolyl, 2,5-dichlorophenyl, 4-(2-methoxy-ethyl)-phenyl, 4-aminocarbonylmethyl-phenyl or 2-alkenyloxy-phenyl where the alkenyl group has 2 to 4 carbon atoms; and
R$^{10}$ is C$_1$ to C$_4$ alkyl, in admixture with a pharmaceutically acceptable additive, wherein the compound of formula I is a hypotensive potentiating agent present in an effective amount to potentiate the β receptor blocking compound of formula V.

9. A method of treating hypertension in animal subjects which comprises administering an antihypertensive effective amount of the composition defined in claim 8.

10. A pharmaceutical composition with hypotensive effect, comprising a compound of the formula I or a pharmaceutically acceptable salt thereof

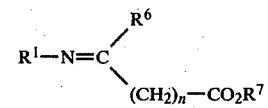

wherein
R$^1$ is 3-chloro-6-pyridazinyl-amino, 3-methyl-6-pyridazinyl-amino, or 3-carbamoyl-6-pyridazinyl-amino;
R$^6$ is C$_1$ to C$_4$ alkyl;
R$^7$ is hydrogen or C$_1$ to C$_4$ alkyl; and
n is an integer of 1 to 3, and a β receptor blocking compound of the formula V or a pharmaceutically acceptable salt thereof

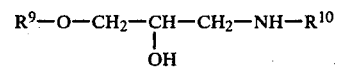

wherein R$^9$ is naphthyl, 4-indolyl, 2,5-dichlorophenyl, 4-(2-methoxy-ethyl)-phenyl, 4-aminocarbonylmethyl-phenyl or 2-alkenyloxy-phenyl where the alkenyl group has 2 to 4 carbon atoms; and
R$^{10}$ is C$_1$ to C$_4$ alkyl, in combination with a pharmaceutically acceptable additive, wherein the compound of formula I is a hypotensive potentiating agent present in an effective amount to potentiate the β receptor blocking compound of formula V.

11. A method of treating hypertension in animal subjects which comprises administering an antihypertensive amount of the composition defined in claim 10.

12. A pharmaceutical composition with hypotensive effect, comprising a compound of the formula I or a pharmaceutically acceptable salt thereof

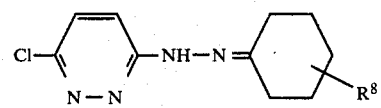

wherein
R$^8$ is 1-carbethoxy or 2,2-dimethyl and a β receptor blocking compound of the formula V or a pharmaceutically acceptable salt thereof

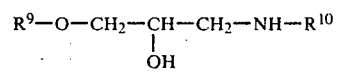

wherein $R^9$ is naphthyl, 4-indolyl, 2,5-dichlorophenyl, 4-(2-methoxy-ethyl)-phenyl, 4-aminocarbonylmethylphenyl or 2-alkenyloxy-phenyl where the alkenyl group has 2 to 4 carbon atoms; and $R^{10}$ is $C_1$ to $C_4$ alkyl in admixture with a pharmaceutically acceptable additive, wherein the compound of formula I is a hypotensive potentiating agent present in an effective amount to potentiate the $\beta$ receptor blocking compound of formula V.

13. A method of treating hypertension in animal subjects which comprises administering an antihypertensive effective amount of the composition defined in claim 12.

* * * * *